United States Patent [19]

Yukl

[11] 4,102,347

[45] Jul. 25, 1978

[54] ELECTRONIC PAIN CONTROL SYSTEM

[76] Inventor: Tex N. Yukl, 1905 SW. Cedar Hills Blvd., Portland, Oreg. 97225

[21] Appl. No.: 747,352

[22] Filed: Dec. 3, 1976

[51] Int. Cl.² .............................................. A61N 1/36
[52] U.S. Cl. ................................. 128/421; 128/2.1 P
[58] Field of Search ................ 128/2.1 P, 419 R, 421, 128/422, 423

[56] References Cited

U.S. PATENT DOCUMENTS

| | | | |
|---|---|---|---|
| 3,489,152 | 1/1970 | Barbara | 128/422 |
| 3,521,641 | 7/1970 | Farensbach | 128/422 |
| 3,797,500 | 3/1974 | Porter | 128/422 |
| 3,835,833 | 9/1974 | Limoge | 128/422 |

Primary Examiner—William E. Kamm
Attorney, Agent, or Firm—Kolisch, Hartwell, Dickinson & Stuart

[57] ABSTRACT

A constant current supply circuit including a changeable-level compliance voltage source whose output voltage is automatically reduced whenever the impedance of a load connected to the circuit exceeds a predetermined value. A sampling resistor is provided in the path for load current, and this resistor, with load current flowing, develops a related voltage whose level is employed directly to affect the operating level of the compliance voltage source.

6 Claims, 1 Drawing Figure

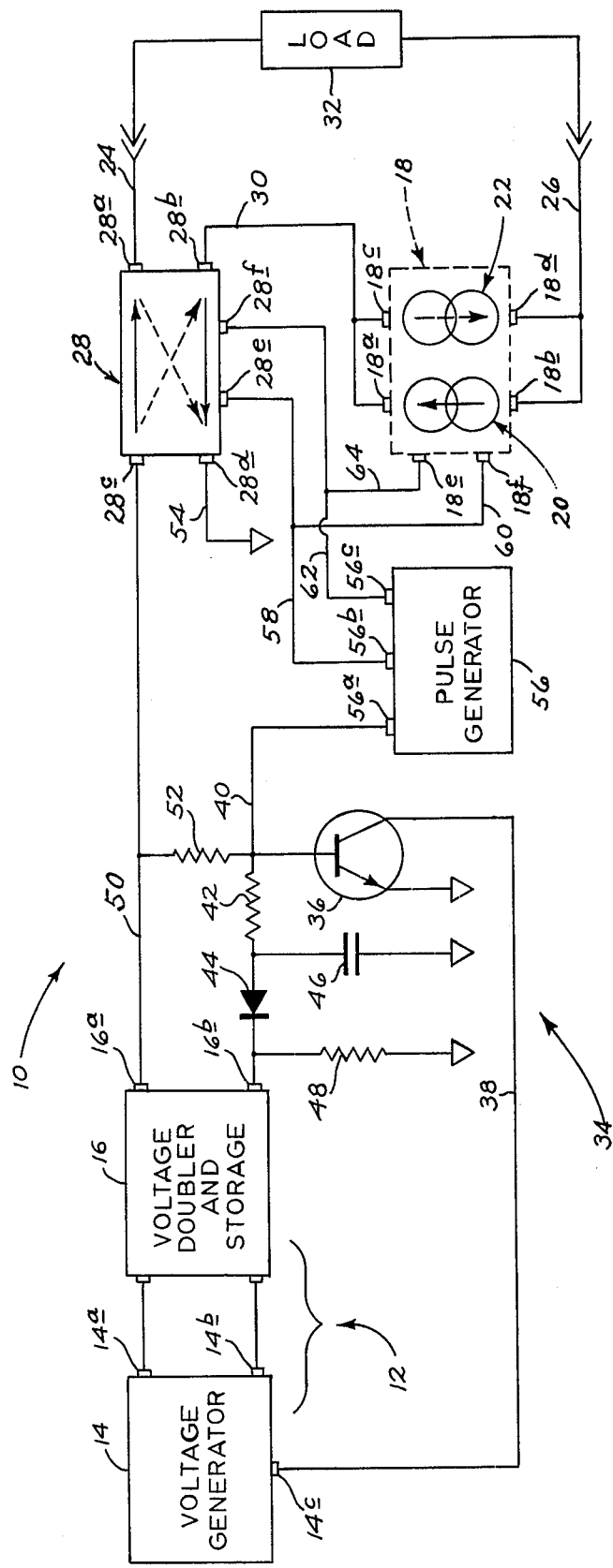

4,102,347

ELECTRONIC PAIN CONTROL SYSTEM

BACKGROUND AND SUMMARY OF THE INVENTION

This invention pertains to a current supply circuit, and more particularly, to such a circuit which includes changeable-level voltage source for the supply of current, the level of which source is varied in accordance with the impedance of a load connected to the circuit. For the purpose of illustration herein, a preferred embodiment of the circuit is described in connection with transcutaneous stimulation which is used for pain relief purposes. In such apparatus, the instant invention has been found to have particular utility.

Speaking in very general terms, a conventional current supply circuit includes a current source connected in series with what is known as a compliance voltage source. These two devices are connected in series between a pair of output terminals adapted for connection to a load. Typically, the compliance voltage source operates at a particular maximum voltage, which voltage is divided between the current source and the output terminals directly in accordance with the impedance of any load connected to the output terminals. The larger the impedance value of a connected load, the more of the compliance voltage which appears across the load and the less of it which appears across the current source. The lower the impedance value of a load, the smaller the voltage across the load and the larger the voltage across the current source. The sum of the voltages across the load and the current source always substantially equals the maximum voltage level of the compliance voltage source.

While there are applications where this kind of an arrangement is entirely satisfactory, there are many others where it is desirable to reduce and limit the maximum voltage which can appear across output terminals in such a supply circuit. One of these applications concerns devices known as transcutaneous stimulators which, essentially, are pulsed current supply circuits intended for connection through electrodes to a person's skin for the purpose of creating electrical current nerve stimulation. Such a device is used quite frequently for pain relief. However, it is known that it is possible for too high a voltage between output electrodes to cause skin damage. Further, if too high a voltage exists between such electrodes in their open-circuited condition, then, if a stimulator, while turned on, is connected to a person's skin, a substantial shock can occur.

A general object of the present invention is to provide a current supply circuit which includes a changeable-level compliance voltage source whose voltage output level is modified in accordance with the impedance of a load connected to the circuit.

More particularly, the present invention proposes a circuit wherein, so long as the value of the impedance of a connected load is below a predetermined maximum value, the overall circuit performs essentially like an ordinary current supply circuit of the type generally described above. However, on the connected load exceeding this predetermined maximum impedance value, a control subcircuit, which is included in the circuit, responds to this condition quickly to shut down the level of the voltage in the compliance voltage source to an acceptable minimal level, which level remains until the impedance value of any connected load is again below the predetermined maximum impedance value.

With this kind of arrangement, the open-circuit voltage which exists between output terminals in such a supply circuit when the same is turned on, is the minimum voltage level just mentioned, and there is no likelihood of a shock occurring when electrodes are connected to a person. Further, if, when electrodes are connected, the skin impedance between the electrodes exceeds the predetermined maximum impedance value, the compliance voltage level is held at the minimum voltage level so that no skin damage can occur.

These and other objects and advantages which are attained by the invention will become more fully apparent as the description which now follows is read in conjunction with the accompanying single drawing figure.

DESCRIPTION OF THE DRAWING

The single drawing figure is a schematic diagram, partly in block form, illustrating the construction of a portion of a transcutaneous stimulator including a current supply circuit constructed in accordance with the present invention.

DETAILED DESCRIPTION OF THE INVENTION

Turning now to the drawing, indicated at 10 is a portion of a transcutaneous stimulator including a current supply circuit made in accordance with the present invention. Shown at 12 is a changeable-level compliance voltage source, including a conventional voltage generator, indicated in block form at 14, and a conventional voltage doubler and storage circuit, indicated in block form at 16. Generator 14 takes the form herein of a changeable-amplitude high-frequency oscillator which produces high-frequency AC between output terminals 14a, 14b. An amplitude-change control terminal 14c is provided for the generator. Changes in voltage on terminal 14c effect changes in the amplitude of the AC voltage developed between terminals 14a, 14b. More specifically, the higher the voltage on terminal 14c, the higher the voltage between terminals 14a, 14b, up to a maximum of about one-hundred volts AC, peak-to-peak. When terminal 14c is grounded, the voltage between terminals 14a, 14b drops to about ten volts AC, peak-to-peak. The output terminals of the voltage generator are connected to the input terminals doubler and storage circuit 16. This circuit produces, between terminals 16a, 16b, a changeable-level DC output voltage that ranges between about ten volts DC and about one-hundred volts DC. Such voltage is referred to herein as a compliance voltage.

Indicated by a dashed block 18 is a changeable-level constant current source which is also of conventional construction. Shown within block 18, schematically, are symbols representing two current generators 20, 22, wherein arrows are used to indicate the respective orientations for producing current flow in opposite directions. A solid arrow is used in generator 20, and a dashed arrow in generator 22. When generator 20 is switched on, as will be explained, it couples to output terminals 18a, 18b in block 18. Similarly, when generator 22 is switched on, it couples to output terminals 18c, 18d.

It should be understood that while source 18 has just been described as one including a pair of oppositely directed current generators, such an arrangement would typically be constructed using a single generator, with appropriate switching circuitry provided which effectively changes the direction in which current flows at output terminals connected to the source. There are many ways of constructing such a source, and none of them forms any part of the present invention.

Control terminals 18e, 18f are provided for block 18. With a certain positive voltage existing on terminal 18e, and a substantially zero voltage existing on terminal 18f, generator 20 operates. With essentially the same certain positive voltage existing on terminal 18f, and a substantially zero voltage existing on terminal 18e, generator 22 operates. Under other circumstances, there is no current flow through source 18.

As was previously mentioned, another aspect of current source 18 is that its level can be changed. For example, it is contemplated in the construction shown that an output current level for this source is infinitely selectable in the range from about zero to about thirty milliamperes. This is a range of currents which has been found to be particularly suitable for the usual transcutaneous stimulation procedure. A suitable means (not shown) is provided for selecting such a current level.

Further included in circuit 10 are two output terminals 24, 26. Terminal 24 is connected to a terminal 28a in a switching circuit 28, the function of which will be explained shortly. Terminal 26 is connected to each of terminals 18b, 18d in the current source. Terminals 18a, 18c in the current source are connected through a conductor 30 to another terminal 28b in switching circuit 28. Terminals 24, 26 herein are adapted for connection, through suitable body-contacting electrodes, to a person's skin, represented in the figure by block 32 designated "LOAD".

Contained in circuit 10, in accordance with the invention, is a voltage-level control means which functions, as will be explained, to change the level of the compliance voltage produced by source 12. This voltage-level control means is designated generally at 34, and includes a transistor 36. The emitter of transistor 36 is connected to the circuit ground (represented by a triangle), and the collector is connected through a conductor 38 to previously mentioned control terminal 14c in generator 14. The base of transistor 36 connects with a conductor 40 which connects through a resistor 42 and a diode 44 to output terminal 16b in block 16. The anode of diode 44 connects to the circuit ground through a capacitor 46, and the cathode of the diode connects to the circuit ground through a resistor 48.

Terminal 16a in block 16 connects through a conductor 50 to a terminal 28c in switching circuit 28. A resistor 52 interconnects conductors 40, 50. A conductor 54 connects yet another terminal, 28d, in circuit 28 to the circuit ground.

In the setting of transcutaneous stimulation, it has been found to be desirable to supply current to a patient in pulses at a rate of around 100-pulses-per-second. More specifically, it has been found to be desirable to apply, first, a pulse of one polarity for a selected time duration, such as about 0.2-milliseconds, followed immediately by an equal current pulse in the opposite direction for substantially the same duration — with such "bidirectional" pulses applied at the above-mentioned rate. It will be obvious that other kinds of current supplies for other applications will not require this pulsing technique. However, in the circuit shown in the drawing there is provided a pulse generator 56 including output terminals 56a, 56b, 56c which function, as will be described, to generate pulses like those just discussed. Terminal 56a connects with previously mentioned conductor 40. Terminal 56b connects through a conductor 58 with a terminal 28e in switching circuit 28, and through conductor 58 and a conductor 60 with previously mentioned terminal 18f. Terminal 56c connects through a conductor 62 with a terminal 28f in circuit 28, and through conductor 62 and a conductor 64 with previously mentioned terminal 18e.

Pulse generator 56 is of conventional construction. When it operates, it produces at terminal 56a, positive-going square-wave pulses lasting about 0.4-milliseconds, at a rate of about 100-pulses-per-second. On terminal 56b it produces similar positive-going square-wave pulses, approximately 0.2-milliseconds long, and corresponding in time to the first 0.2-millisecond portions of the pulses produced on terminal 56a. On terminal 56c the pulse generator produces positive-going square-wave pulses, each also lasting about 0.2-millisecond, and each corresponding in time to the latter 0.2-millisecond portions of the pulses produced on terminal 56a.

Explaining generally how the pulse generator cooperates with other elements in circuit 10, each pulse on terminal 56a turns on transistor 36, and thereby causes grounding, through the transistor, of conductor 38, and hence of control terminal 14c in generator 14. Each pulse on terminal 56b produces switching in circuit 28 whereby flow can take place through this circuit as indicated by the dashed arrows in block 28. Also, each such pulse acts through terminal 18f to cause current flow through source 18 as indicated by generator 22. Each pulse on terminal 56c causes switching in 28 whereby flow can take place therethrough as indicated by the solid arrows in block 28. Also, each such pulse on terminal 56c acts through terminal 18e to cause current flow through source 18 as indicated by generator 22.

As was previously mentioned, source 18 is infinitely variable to select output current levels within the range of about zero to about thirty milliamperes. This range has been selected as the one most suitable for the usual transcutaneous stimulation procedure. Different specific levels are, of course, selected for different stimulation situations. Further, generator 14 and circuit 16 have been constructed herein to produce a compliance voltage between output terminals 16a, 16b of up to about one-hundred volts DC. This has been found to be a desirable maximum level. Whenever transistor 36 is in a nonconducting state, substantially the full maximum amount of this compliance voltage appears between terminals 16a, 16b. However, whenever the transistor conducts and grounds terminal 14c, the output level of voltage generator 14 is reduced, as will be explained, to lower the available compliance voltage.

Under circumstances with no load connected to terminals 24, 26, and with circuit 10 operating, transistor 36 is biased to a stage of conduction, by virtue of the voltage made available at its base, which maintains generator 14 operating at a sufficient level to produce a compliance voltage between terminals 16a, 16b also of about ten volts DC. Substantially this same voltage appears periodically between terminals 24, 26 with operation of pulse generator 56. Thus, the open-circuit voltage appearing between terminals 24, 26 is relatively low.

According to an important feature of the invention, so long as the impedance value of a load connected between terminals 24, 26 is less than about 3000-ohms, circuit 10 always functions to create a compliance voltage level related to the amount of current flowing through the load, which acts as if there is a constant fixed impedance of 3000-ohms connected between conductors 40, 50. In other words, so long as the connected load does not exceed the value just mentioned, and with a particular level of current selected from source 18, the compliance voltage produced by source 12 will be automatically adjusted to a value whereby the ratio of this voltage and the selected current equals 3000-ohms.

Let us take a typical operation for example. With circuit 10 operating, let us assume that electrodes connected to terminals 24, 26 are attached to a person's skin, and that the impedance between these electrodes (through the skin) is 1000-ohms. Let us assume further that source 18 has been adjusted to provide a maximum current of ten milliamperes. Initially, and because of a certain minimum voltage required to keep the current source operating, only a portion of the original open-circuit ten volts appears across the load, and this portion produces a current which, it will be recalled, can only flow during the time that a pulse exists either on terminal 56b or on terminal 56c. Assuming that initial flow is as produced by current generator 20, this flow is into conductor 30 through switching circuit 28 and conductor 54 to the circuit ground. From circuit ground, current flows through resistor 48, through voltage source 12 to conductor 50, back through switching circuit 28, and through the load back to the current generator.

The consequence of this activity is that a negative voltage builds up at the junction between capacitor 46 and resistor 42, which voltage tends to hold transistor 36 in a nonconducting state. It should be pointed out that whenever a pulse exists on pulse generator terminal 56a, the transistor is held in a conducting state, which situation results in the output voltage of generator 14 being held down. However, and considering the time that no pulse exists on terminal 56a, the voltage at the base of the transistor which is effective to control whether it is turned on or off depends upon the voltages existing at the junction just mentioned between resistor 42 and capacitor 46, and that existing at the junction between resistor 52 and conductor 50. With some negative voltage applied to the base sufficient to hold the transistor in a nonconductive state, generator 14 operates to build up the voltage between terminals 16a, 16b, which results in a slightly greater current flow occurring through the load with the next set of control pulses from terminals 56b, 56c.

So long as current through the load is building up to the ten milliampere setting mentioned earlier, a sufficiently negative voltage is maintained on the base of the transistor, during times that no pulse exists on terminal 56a, to allow the voltage of source 12 to build up. When the full ten milliampere current can flow and is flowing, the compliance voltage which exists between terminals 16a, 16b is thirty volts. This results in the previously mentioned constant impedance of 3000-ohms which the circuit "assumes" is connected between conductors 40, 50. Without any change occurring in load resistance, or in the setting of current source 18, this situation remains unchanged. As a consequence, and in repeated cycles, a 0.2-millisecond positive-going current pulse, at the level of ten milliamperes, is delivered to the person, followed immediately by a negative-going pulse of the same duration and level, followed by a period of 9.6-milliseconds with no current so delivered. It might be pointed out that this manner of delivering pulses has been found to be the most effective for nerve stimulating and the least damaging to skin tissue.

Should the load impedance change at any time during this operation, and so long as it does not exceed 3000-ohms, current continues to be delivered in the manner just described and at the ten milliampere level called for. All that takes place is that the division of compliance voltage between the current source and the load changes. The sum of the voltages across the current source and across the load will, under these circumstances, always equal the full value of the compliance voltage which is then being used. In the case now being illustrated this value is thirty volts.

The fact that load current flows through resistor 48 causes this resistor to act as a monitoring resistor which, in effect, and inasmuch as the current level is constant, provides a direct indication of load impedance. As was discussed above, an equilibrium condition is reached whereby the negative voltage at the junction between resistor 42 and capacitor 46 balances with voltage on conductor 50 so as to produce a control voltage on the base of transistor 36 sufficient to maintain the compliance voltage at thirty volts.

If the setting of the current source is changed, for example to twenty milliamperes, load current builds in the manner described previously, and a new equilibrium condition is reached whereby transistor 36 controls source 12 so as to produce a compliance voltage of sixty volts. With the full level of current selected, i.e., thirty milliamperes, the compliance voltage builds up to ninety volts.

Should the load impedance exceed 3000-ohms, then what will occur is that the current source, at the compliance voltage level then called for by the particular current level setting, will not be able to supply the full level of called-for current. As a consequence, a slightly lower value of current than the setting value will flow in the circuit, and this will result in the base voltage of the transistor rising. This will increase conduction in the transistor, and effect a lowering of the compliance voltage. With a drop in compliance voltage level, yet a smaller current flows, and this process continues in a regenerative fashion until the compliance voltage has been reduced to the minimum level of about ten volts. As a consequence, a potential damage situation does not occur in the person's skin.

It will thus be apparent that resistor 48 acts as a means for monitoring load current, and ultimately load impedance. The negative voltage which exists across this resistor is stored in capacitor 46, and is applied through resistor 42 to the base of transistor 36, tending to turn the transistor off. Also acting on the transistor's base, and tending to turn the transistor on, is a positive voltage derived directly from the compliance voltage, and applied through resistor 52. The larger the negative voltage across resistor 48, the larger is the compliance voltage; and the ratio of the resistance values of resistors 42, 52 determines what level of compliance voltage will develop with respect to a given negative voltage across resistor 48. Herein, this ratio is selected to produce a compliance voltage which, when divided by the current flowing in the load, equals 3000-ohms. Those skilled in the art will readily appreciate how such a ratio may be changed to handle other circumstances.

There is thus provided by the invention a unique current supply circuit in which control occurs automatically for the level of compliance voltage, so that the voltage which is applied to any connected load is not only limited to a predetermined maximum level, but is in fact shut down when a too-high load impedance tends to call for an excessive voltage. This same control also insures that open-circuit voltage is low.

It is appreciated that the circuit of the invention may be used in a number of applications other than in the setting of a transcutaneous stimulator. For example, it can certainly be used in a variety of current supply circuits which are neither pulse nor bidirectional.

Thus, while a preferred embodiment of the invention has been described herein, it is appreciated that variations and modifications may be made without departing from the spirit of the invention.

It is claimed and desired to secure by Letters Patent:

1. A current supply circuit comprising
   a pair of output terminals adapted for connection to a load,
   a current source operatively connected to said terminals for supplying current to a load connected therebetween,
   a changeable-level voltage source for and operatively connected both to said current source and to said terminals, and
   voltage-level control means operatively connected both to said output terminals and to said voltage source for sensing the impedance value of any load connected between said terminals, and for changing the level of voltage produced by said voltage source in accordance with the value of such sensed impedance.

2. The circuit of claim 1, wherein said control means includes means for monitoring the level of current flowing through a load connected between said terminals.

3. A current supply circuit comprising
   a pair of output terminals adapted for connection to a load,
   a current source operatively connected to said terminals for supplying current to a load connected therebetween,
   a changeable-level voltage source for and operatively connected both to said current source and to said terminals, and
   voltage-level control means operatively connected both to said output terminals and to said voltage source for sensing the impedance value of any load connected between said terminals, and for reducing the level of voltage produced by said voltage source with such impedance value exceeding a predetermined impedance value.

4. The circuit of claim 3, wherein said control means includes means in series circuit with said output terminals for monitoring the level of current flowing to a load connected between the terminals.

5. A constant current supply circuit comprising
   a pair of output terminals adapted for connection to a load,
   a selectively changeable-level constant current source operatively connected to said terminals for supplying current at different selected levels to a load connected between the terminals,
   a changeable-level voltage source for and operatively connected both to said current source and to said terminals, and
   voltage-level control means operatively connected both to said output terminals and to said voltage source for sensing the impedance value of any load connected between said terminals, and for reducing the level of voltage produced by said voltage source with such impedance value exceeding a predetermined impedance value.

6. The circuit of claim 5, wherein said control means includes means in series circuit with said output terminals for monitoring the level of current flowing to a load connected between the terminals.

* * * * *